United States Patent [19]

Hiltebrandt et al.

[11] 4,452,546
[45] Jun. 5, 1984

[54] COUPLING MEMBER FOR COUPLING AN OPTICAL SYSTEM TO AN ENDOSCOPE SHAFT

[75] Inventors: Siegfried Hiltebrandt; Ludwig Bonnet, both of Knittlingen, Fed. Rep. of Germany

[73] Assignee: Richard Wolf GmbH, Knittlingen, Fed. Rep. of Germany

[21] Appl. No.: 325,760

[22] Filed: Nov. 30, 1981

[51] Int. Cl.³ .................... B25G 3/16; F16B 7/20; F16D 1/00
[52] U.S. Cl. .................... 403/349; 403/327; 403/329
[58] Field of Search ............... 403/348, 349, 325, 327, 403/329, 111; 354/62; 285/308, 317

[56] References Cited

U.S. PATENT DOCUMENTS

| 3,493,253 | 2/1970 | Deplante | 403/348 |
| 3,858,910 | 1/1975 | Oetiker | 403/349 X |
| 3,874,803 | 4/1975 | Svensson | 403/329 X |
| 4,305,386 | 12/1981 | Tawara | 354/62 X |

Primary Examiner—Wayne L. Shedd
Attorney, Agent, or Firm—Kinzer, Plyer, Dorn & McEachran

[57] ABSTRACT

This invention relates to coupling members for coupling an optical system to an endoscope shaft, of the kind comprising a locking ring whose proximal terminal surface has an excision through which may pass an annular collar of the optical system insertible into the shaft, and having a radial guiding stud which is engagable in a groove or slot of the shaft provided with an inclination and which, by twisting out of the insertion position of the optical system, couples the optical system to the shaft in the manner of a bayonet joint. According to this invention, the locking ring has an internal annular groove arranged to receive a spring bent into a circular or partially circular shape and bearing against the bottom of the groove. One end of the spring is connected to the locking ring and the other end of the spring is connected to the shaft. When the annular collar is inserted in the locking ring, the spring is reduced in circumference and is stressed by rotation of the locking ring. The spring may have an undulant outline or be formed as a leaf spring.

3 Claims, 7 Drawing Figures

COUPLING MEMBER FOR COUPLING AN OPTICAL SYSTEM TO AN ENDOSCOPE SHAFT

BACKGROUND OF THE INVENTION

The present invention relates to coupling members for coupling an optical system to an endoscope shaft, of the kind comprising a locking ring whose proximal terminal surface has an excision through which may pass an annular collar of the optical system insertible into the shaft, and a radial guiding stud which engages in a groove or slot of the shaft provided with an inclination and which, by twisting out of the insertion position of the optical system couples the latter to the endoscope shaft in the manner of a bayonet joint. Hereinafter such a coupling member will be referred to as "of the kind described".

Commonly known coupling members of the kind described may be released in particular circumstances during manipulation of the endoscope by accidental twisting of the locking ring, or the turning of the locking ring into the coupled position may have been omitted by inadvertence. The risk then arises that the costly optical system may slide out of the shaft and may in particular circumstances be destroyed or damaged by dropping on to the floor.

It is an object of the invention to provide a construction in which the locking ring is always brought into its coupling position and is secured against accidental twisting in the direction causing disengagement of the coupling.

SUMMARY OF THE INVENTION

Accordingly, the invention consists in a coupling member of the kind described, wherein said locking ring has an internal groove arranged to receive a spring bent into an at least partially circular shape and bearing against the bottom of said groove, one end of said spring being connected to said locking ring and the other end of said spring being connected to said shaft, said spring being reduced in circumference when said annular collar is inserted into said locking ring and being stressed by rotation of said locking ring.

In using the coupling member, the optical system is inserted into the shaft, whereby the circumference of the spring is reduced and is thus no longer bearing with frictional locking contact against the bottom of the internal annular groove. It is only in this position that the annular collar of the optical system may be inserted through the excision of the locking ring. After the annular collar has passed through the terminal face of the locking ring, the latter is released and the locking ring is turned back by virtue of the loading of the spring, if appropriate complementarily by manual rotation, and in doing so the spring expands again and bears in frictional locking manner against the base surface of the annular groove of the locking ring, so that powerful twisting only of the locking ring against the action of the spring becomes possible for freeing the coupling or joint under reduction of the spring circumference. Any accidental turning of the locking ring will thus always be counteracted immediately against the direction of joint release by means of the spring tensioned thereby, so that a release of the optical system from the shaft is possible only by a deliberate manual rotation of the locking ring.

BRIEF DESCRIPTION OF THE DRAWINGS

In order that the invention may be more clearly understood, reference will now be made to the accompanying drawings which show certain embodiments thereof by way of example and in which.

SPECIFIC DESCRIPTION OF THE PREFERRED EMBODIMENTS

Figure 7:
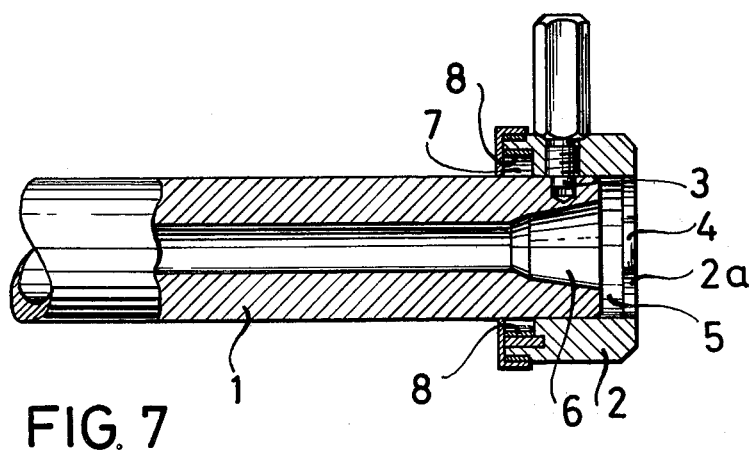
FIG. 7 shows an axial cross-section according to one of the FIGS. 1 to 6.

Referring now to the drawings, as a rule, a locking ring 2 is fitted on the proximal end of an endoscope shaft 1 with limited rotatability and small axial displaceability. A radially inwardly directed guiding or locating pin 3 (FIG. 7) engages in a groove or slot of the shaft having a shallow gradient towards the distal end. The proximal end surface 2a of the locking ring 2 has a passage 4 for the insertion of an optical system, which is not illustrated, through the shaft 1, and an excision starting from this passage 4 and through which an external annular collar of the optical system may pass into the space 5 behind the near side end surface of the locking ring 2. Upon turning the locking ring 2, the annular collar passes behind the end surface 2a and a taper of the optical system is thrust during this rotation into a tapered recess 6 of the shaft 1, since the locking ring 2 also performs a small axial displacement in the direction towards the far side whilst being turned.

Figure 1:
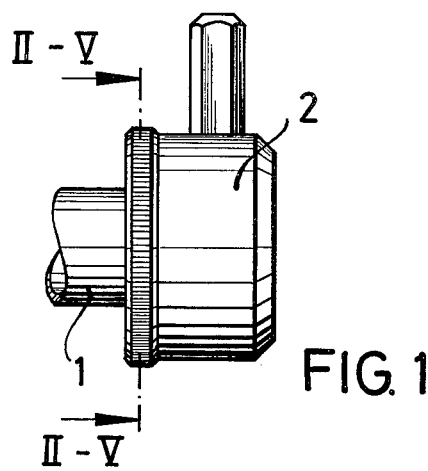
FIG. 1 shows a side view of the proximal end of an endoscope shaft.
Figure 2:
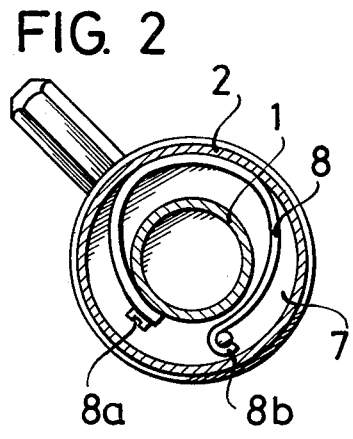
FIGS. 2, 3, 4 and 5 show cross-sections along the line II–V of FIG. 1 with different constructions of and fastenings for the spring.
Figure 3:
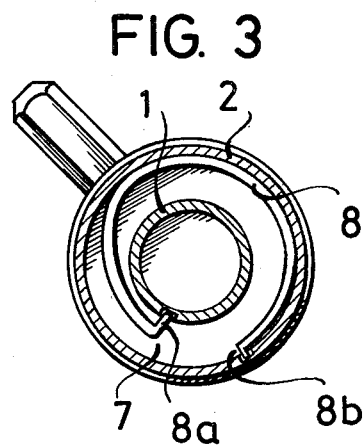

To prevent the initially referred to accidental freeing of the joint or turning of the locking ring, a locking ring 2 according to the invention is provided with an internal annular groove 7 which in accordance with FIGS. 2 and 3 receives a spring 8 bent into wholly or partially circular shape. One end 8a of the spring 8 is firmly secured to the shaft 1 and the other end 8b is secured to the locking ring 2, e.g. as shown in FIG. 2 or FIG. 3. By virtue of its shape, this spring 8 has the natural tendency to expand or widen so that the locking ring 2 is turned with respect to the shaft 1 into a position in which the annular collar of the optical system is covered within the space 5 of the locking ring by the end wall 2a, and the taper of the optical system is thrust into the tapered recess 6. The spring 8 is so arranged for this purpose that it bears with friction under a particular tension against the base of the annular groove 7 in the aforesaid locked or coupled position of the optical system and shaft, and this establishes a blocking action against turning the locking ring 2 in the direction causing freeing of the joint, which may be overcome by manual action only.

In order that the optical system may be coupled to the shaft, the locking ring 2 has to be turned manually into a position in which the annular collar of the optical system may be inserted through the excision of the end surface of the locking ring into the space 5. This rotation lifts the spring 8 off the bottom of the annular groove 7 since it is stressed and thereby simultaneously reduced in circumference. As soon as the locking ring 2 or its grip is released, it is turned by the spring 8 with respect to the shaft 1 and the spring will be relieved except for a small remanent initial loading and will be expanded so that it is again brought to bear under friction against the bottom of the annular groove 7 and thereby represents a lock against rotation of the locking ring and freeing of the joint.

Figure 4:
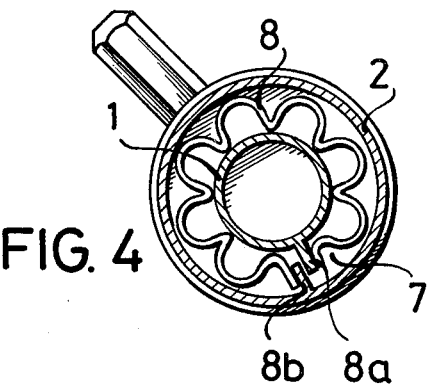
Figure 5:
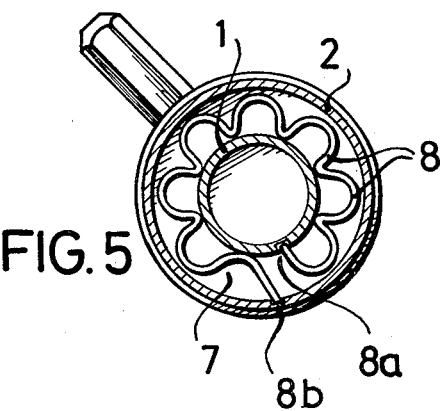
Figure 6:
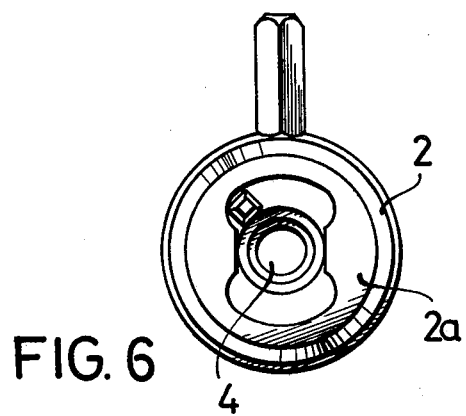
FIG. 6 shows a proximal end view of the locking ring.

The spring may simply be formed in the manner of a leaf spring 8, as shown in FIGS. 2 and 3, or it may also have an undulant outline according to FIGS. 4 and 5, the ends bearing on stops according to FIG. 4, or engaging in recesses according to FIG. 5, or being secured by screws or the like. In the case of an undulant configuration of the spring, this provides a whole series of contact points with the bottom of the annular groove 7, thereby increasing the friction which may complementarily be increased by utilisation of a leaf spring and thereby prevents accidental turning back of the locking ring or a release of the joint. In another embodiment of the coupling member, it may be sufficient in some cases to stress the locking ring 2 solely by spring force without in addition causing friction of the spring 8 against the bottom of the annular groove 7 to prevent accidental turning of the locking ring 2 thereby, which may simply be accomplished by displacement of the points of action 8a, 8b of the spring.

I claim:

1. In a coupling member for coupling an optical system to an endoscope shaft, comprising a locking ring complementally fitted to the proximal end of said shaft, said locking ring being rotatable on the shaft from a locking position to an insertion position and having a proximal terminal surface presenting an opening of such irregular outline that when the ring is rotated to said insertion position a collar of the optical system is insertible through said opening incidental to locating the optics in said shaft, by rotation of the locking ring out of the insertion position of the optical system, couples said optical system collar to said shaft in the manner of a bayonet joint, the improvement comprising said locking ring being provided with an internal groove in which is located an annular spring bent into an at least partially circular shape said spring bearing at least partially against the bottom of said groove, one end of said spring being connected to said locking ring and the other end of said spring being connected to said shaft so that the spring is stressed by said locking ring rotation toward the insertion position and is stressed sufficiently so that, whereby upon releasing the locking ring after insertion of the optics the stressed spring will rotate the locking ring in the opposite direction to couple the shaft and optics in the manner of said joint with the spring then bearing at least partly against the bottom of said annular groove.

2. A coupling member according to claim 1, wherein said spring has an undulant outline.

3. A coupling member according to claim 1, wherein said spring is formed as a leaf spring.

* * * * *